US008841227B2

(12) United States Patent
Sangar et al.

(10) Patent No.: US 8,841,227 B2
(45) Date of Patent: Sep. 23, 2014

(54) PRODUCTION OF AROMATICS FROM METHANE

(75) Inventors: Neeraj Sangar, League City, TX (US); Jocelyn A. Kowalski, Mullica Hill, NJ (US); Larry L. Iaccino, Seabrook, TX (US); Kenneth R. Clem, Humble, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 428 days.

(21) Appl. No.: 12/863,467

(22) PCT Filed: Dec. 22, 2008

(86) PCT No.: PCT/US2008/087980
§ 371 (c)(1),
(2), (4) Date: Aug. 30, 2010

(87) PCT Pub. No.: WO2009/097067
PCT Pub. Date: Aug. 6, 2009

(65) Prior Publication Data
US 2010/0331592 A1    Dec. 30, 2010

Related U.S. Application Data

(60) Provisional application No. 61/023,976, filed on Jan. 28, 2008.

(51) Int. Cl.
  *B01J 29/06*    (2006.01)
  *B01J 37/08*    (2006.01)
  *C07C 2/76*     (2006.01)
  *B01J 35/00*    (2006.01)
  *B01J 29/076*   (2006.01)
  *B01J 29/48*    (2006.01)
  *B01J 37/00*    (2006.01)
  *B01J 21/06*    (2006.01)

(52) U.S. Cl.
  CPC  *B01J 29/48* (2013.01); *B01J 37/08* (2013.01); *C07C 2/76* (2013.01); *C10G 2400/30* (2013.01); *B01J 2229/20* (2013.01); *B01J 35/0006* (2013.01); *B01J 35/002* (2013.01); *B01J 21/066* (2013.01); *B01J 29/076* (2013.01); *B01J 21/063* (2013.01); *C07C 2529/48* (2013.01); *B01J 2229/42* (2013.01); *B01J 37/0009* (2013.01); *C10G 2300/1025* (2013.01)
  USPC .................. 502/77; 502/60; 502/63; 502/64; 502/71; 502/78; 502/79

(58) Field of Classification Search
  USPC ................ 502/60, 63, 64, 71, 77, 78, 79
  See application file for complete search history.

(56) References Cited

U.S. PATENT DOCUMENTS

| | | | | |
|---|---|---|---|---|
| 4,072,731 A | * | 2/1978 | Rausch | 208/139 |
| 4,297,243 A | * | 10/1981 | Moorehead | 502/77 |
| 4,388,224 A | * | 6/1983 | Moorehead | 502/60 |
| 4,727,206 A | | 2/1988 | Clayson et al. | |
| 5,026,937 A | | 6/1991 | Bricker | |
| 5,182,242 A | | 1/1993 | Marler | |
| 5,336,825 A | | 8/1994 | Choudhary et al. | |
| 5,430,000 A | | 7/1995 | Timken | |
| 5,905,051 A | | 5/1999 | Wu et al. | |
| 6,037,294 A | * | 3/2000 | Drake et al. | 502/64 |
| 6,114,268 A | * | 9/2000 | Wu et al. | 502/74 |
| 6,235,955 B1 | * | 5/2001 | Yao et al. | 585/418 |
| 6,239,057 B1 | | 5/2001 | Ichikawa et al. | |
| 6,420,295 B1 | * | 7/2002 | Wu et al. | 502/71 |
| 6,426,442 B1 | | 7/2002 | Ichikawa et al. | |
| 6,617,275 B1 | * | 9/2003 | Sharma et al. | 502/61 |
| 2004/0266608 A1 | | 12/2004 | Long et al. | |
| 2007/0134146 A1 | * | 6/2007 | Bull et al. | 423/239.2 |

FOREIGN PATENT DOCUMENTS

| | | |
|---|---|---|
| TW | 200603890 | 2/2006 |
| WO | 98/51409 | 11/1998 |
| WO | 2005/032713 | 4/2005 |
| WO | 2006/006480 | 1/2006 |
| WO | 2006/068814 | 6/2006 |
| WO | 2007/123808 | 11/2007 |
| WO | 2008/062028 | 5/2008 |

OTHER PUBLICATIONS

Japan Chemical Week, "Benzene Synthesized Directly from Methane: Mitsubishi Chem", vol. 46, No. 2337, ISSN 0047-1755, dated Oct. 6, 2005, The Chemical Daily Co., Ltd.
Honda et al., "Preparation of highly active binder-added $MoO_3$/HZSM-5 catalyst for the non-oxidative dehydroaromatization of methane", Appl. Cat. A: General, 351 (2008) 122-130.

\* cited by examiner

*Primary Examiner* — Elizabeth Wood
(74) *Attorney, Agent, or Firm* — Catherine L. Bell; Amanda K. Jenkins (57) ABSTRACT

A catalyst for the conversion of methane to higher hydrocarbons including aromatic hydrocarbons comprises a support and molybdenum or a compound thereof dispersed on the support. The support comprises an aluminosilicate zeolite combined with a binder selected from silica, titania, zirconia and mixtures thereof. The catalyst is substantially free of aluminum external to the framework of the aluminosilicate zeolite.

10 Claims, 3 Drawing Sheets

PRODUCTION OF AROMATICS FROM METHANE

CROSS-REFERENCE TO RELATED APPLICATIONS

This application is a National Stage Application of International Application No. PCT/US2008/087980 filed Dec. 22, 2008, which claims priority from U.S. Ser. No. 61/023,976 filed Jan. 28, 2008, both of which are incorporated herein by reference.

FIELD

This invention relates to a process for producing aromatic hydrocarbons from methane and, in particular, from natural gas.

BACKGROUND

Aromatic hydrocarbons, particularly benzene, toluene, ethylbenzene and xylenes, are important commodity chemicals in the petrochemical industry. Currently, aromatics are most frequently produced from petroleum-based feedstocks by a variety of processes, including catalytic reforming and catalytic cracking. However, as the world supplies of petroleum feedstocks decrease, there is a growing need to find alternative sources of aromatic hydrocarbons.

One possible alternative source of aromatic hydrocarbons is methane, which is the major constituent of natural gas and biogas. World reserves of natural gas are constantly being upgraded and more natural gas is currently being discovered than oil. Because of the problems associated with transportation of large volumes of natural gas, most of the natural gas produced along with oil, particularly at remote places, is flared and wasted. Hence the conversion of alkanes contained in natural gas directly to higher hydrocarbons, such as aromatics, is an attractive method of upgrading natural gas, providing the attendant technical difficulties can be overcome.

A large majority of the processes currently proposed for converting methane to liquid hydrocarbons involve initial conversion of the methane to synthesis gas, a blend of $H_2$ and CO. However, production of synthesis gas is capital and energy intensive and hence routes that do not require synthesis gas generation are preferred.

A number of alternative processes have been proposed for directly converting methane to higher hydrocarbons. One such process involves catalytic oxidative coupling of methane to olefins followed by the catalytic conversion of the olefins to liquid hydrocarbons, including aromatic hydrocarbons. For example, U.S. Pat. No. 5,336,825 discloses a two-step process for the oxidative conversion of methane to gasoline range hydrocarbons comprising aromatic hydrocarbons. In the first step, methane is converted to ethylene and minor amounts of $C_3$ and $C_4$ olefins in the presence of free oxygen using a rare earth metal promoted alkaline earth metal oxide catalyst at a temperature between 500° C. and 1000° C. The ethylene and higher olefins formed in the first step are then converted to gasoline range liquid hydrocarbons over an acidic solid catalyst containing a high silica pentasil zeolite.

However, oxidative coupling methods suffer from the problems that they involve highly exothermic and potentially hazardous methane combustion reactions and they generate large quantities of environmentally sensitive carbon oxides.

A potentially attractive route for upgrading methane directly into higher hydrocarbons, particularly ethylene, benzene and naphthalene, is dehydroaromatization or reductive coupling. This process typically involves contacting the methane with a catalyst comprising a metal, such as rhenium, tungsten or molybdenum, supported on a zeolite, such as ZSM-5, at high temperature, such as 600° C. to 1000° C.

For example, U.S. Pat. No. 4,727,206 discloses a process for producing liquids rich in aromatic hydrocarbons by contacting methane at a temperature between 600° C. and 800° C. in the absence of oxygen with a catalyst composition comprising an aluminosilicate having a silica to alumina molar ratio of at least 5:1, said aluminosilicate being loaded with (i) gallium or a compound thereof and (ii) a metal or a compound thereof from Group VIIB of the Periodic Table.

In addition, U.S. Pat. No. 5,026,937 discloses a process for the aromatization of methane which comprises the steps of passing a feed stream, which comprises over 0.5 mole % hydrogen and 50 mole % methane, into a reaction zone having at least one bed of solid catalyst comprising ZSM-5, gallium and phosphorus-containing alumina at conversion conditions which include a temperature of 550° C. to 750° C., a pressure less than 10 atmospheres absolute (1000 kPaa) and a gas hourly space velocity of 400 to 7,500 $hr^{-1}$.

Moreover, U.S. Pat. Nos. 6,239,057 and 6,426,442 disclose a process for producing higher carbon number hydrocarbons, e.g., benzene, from low carbon number hydrocarbons, such as methane, by contacting the latter with a catalyst comprising a porous support, such as silica, alumina, zeolite ZSM-5, FSM-16 and mixtures thereof, which has dispersed thereon rhenium and a promoter metal such as iron, cobalt, vanadium, manganese, molybdenum, tungsten or a mixture thereof. After impregnation of the support with the rhenium and promoter metal, the catalyst is activated by treatment with hydrogen and/or methane at a temperature of about 100° C. to about 800° C. for a time of about 0.5 hr. to about 100 hr. The addition of CO or $CO_2$ to the methane feed is said to increase the yield of benzene and the stability of the catalyst.

Further in our International Patent Publication No. WO 2006/068814, published Jun. 29, 2006, we have described a process for converting methane to higher hydrocarbons including aromatic hydrocarbons, the process comprising contacting a feed containing methane with a dehydrocyclization catalyst, conveniently molybdenum, tungsten and/or rhenium or a compound thereof on ZSM-5 or an aluminum oxide, under conditions effective to convert said methane to aromatic hydrocarbons and produce a first effluent stream comprising aromatic hydrocarbons and hydrogen, wherein said first effluent stream comprises at least 5 wt % more aromatic rings than said feed; and reacting at least part of the hydrogen from said first effluent stream with an oxygen-containing species to produce a second effluent stream having a reduced hydrogen content compared with said first effluent stream.

However, the successful application of reductive coupling to produce aromatics on a commercial scale requires the solution of a number of serious technical challenges. For example, the reductive coupling process is both endothermic and thermodynamically limited. Thus the cooling effect caused by the reaction lowers the reaction temperature sufficiently to greatly reduce the reaction rate and total thermodynamic conversion if significant make-up heat is not provided to the process.

In addition, the process tends to produce carbon and other non-volatile materials, collectively referred to as "coke", that accumulate on the catalyst resulting in reduced activity and potentially undesirable selectivity shifts, as well as loss of valuable feedstock. Although the coke can be removed from the catalyst by oxidative or reductive regeneration, this leads to lost production time as well as potential damage to the catalyst. There is therefore interest in developing dehydrocyclization catalysts that exhibit reduced coke selectivity without loss in selectivity to the desired aromatic products.

One particularly active catalyst for the dehydroaromatization of methane is molybdenum on an aluminosilicate zeolite, such as ZSM-5, particularly where the molybdenum is highly dispersed and anchored at Bronsted acid sites in the pores of the zeolite. Such a catalyst normally also includes a refractory binder, typically alumina, to provide the catalyst particles with the requisite size, density and hardness for use in the dehydroaromatization process. However, it has now been found that the alumina binder can interact with molybdenum during catalyst manufacture and use to produce bulk (that is not anchored to zeolite Bronsted acid sites) aluminum molybdate that can have a detrimental impact on the performance of the catalyst. Thus, bulk aluminum molybdate is found to be highly active for methane conversion with essentially 100% conversion to coke. The present invention therefore seeks to provide a catalyst and process for conversion of methane to aromatics in which the alumina binder is replaced by other refractory materials which provide the catalyst with desired physical properties without impairing its catalytic performance and without providing reactive non-framework aluminum.

International Patent Publication No. WO 1998/051409, published Nov. 19, 1998, discloses a catalyst for converting $C_2$ to $C_{16}$ hydrocarbons to olefins and aromatics with a low rate of coke formation, the catalyst comprising an acid treated zeolite, such as ZSM-5, impregnated with zinc and at least one other metal selected from the group consisting of Group 4B, Group 6B, Group 3A, Group 4A and Group 5A of the Periodic Table of Elements. The catalyst can include a binder selected from alumina, silica, alumina-silica, aluminum phosphate, clays and mixtures thereof.

U.S. Published Patent Application No. 2004/266608, published Dec. 30, 2004, discloses a molecular sieve-containing catalyst for cracking hydrocarbons, comprising molecular sieve, refractory inorganic oxide, clay and a metal component, wherein the amount of said molecular sieve is from 1 to 90% by weight, the refractory inorganic oxide is from 2 to 80% by weight, the clay is from 2 to 80% by weight, and the metal component is from 0.1 to 30% by weight, calculated as the oxide of said metal having its maximum valence state, based on the total amount of the catalyst, wherein said metal component exists essentially in a reduction state and is one or more metals selected from the group consisting of metals of Group IIIA (other than aluminum), metals of Group IVA, VA, IB, IIB, VB, VIB and VIIB, and non-noble metals of Group VIII of the Periodic Table. The metal component is conveniently selected from gallium, tin, copper, silver, zinc, vanadium, molybdenum, manganese, iron, and/or cobalt, and refractory inorganic oxide is conveniently selected from alumina, silica, amorphous silica-alumina, zirconia, titanium oxide, boron oxide, and oxides of alkaline earth metal.

SUMMARY

In one aspect, the invention resides a catalyst for the conversion of methane to higher hydrocarbons including aromatic hydrocarbons, the catalyst comprising a support and molybdenum or a compound thereof dispersed on said support, wherein the support comprises an aluminosilicate zeolite combined with a binder selected from silica, titania, zirconia and mixtures thereof, and wherein the catalyst is substantially free of reactive aluminum external to the framework of said aluminosilicate zeolite.

Conveniently, the aluminosilicate zeolite has a silica to alumina mole ratio between about 14 and about 500, such as between about 20 and about 300, for example between about 22 and about 280. In one embodiment, the aluminosilicate zeolite has a Constraint Index between about 1 and about 12, and typically is ZSM-5.

Conveniently, the amount of molybdenum or said compound thereof in the catalyst is between about 0.1 and about 20% by weight of the catalyst based on elemental molybdenum.

Conveniently, the support comprises from about 1 to about 90% of said binder by weight of the support.

Conveniently, the support further comprises a filler, such as silicon carbide. Typically the filler is present in an amount between from about 0.1 to about 60% by weight of the support.

In a further aspect, the invention resides in a process for converting methane to higher hydrocarbons including aromatic hydrocarbons, the process comprising contacting a feed comprising methane with a dehydrocyclization catalyst in a reaction zone under conditions effective to convert said methane to aromatic hydrocarbons, said dehydrocyclization catalyst comprising a support and molybdenum or a compound thereof dispersed on said support, wherein the support comprises an aluminosilicate zeolite combined with a binder, and wherein the binder is substantially free of reactive aluminum.

In yet a further aspect, the invention resides in a process for converting methane to higher hydrocarbons including aromatic hydrocarbons, the process comprising contacting a feed comprising methane with a dehydrocyclization catalyst in a reaction zone under conditions effective to convert said methane to aromatic hydrocarbons, said dehydrocyclization catalyst comprising a support and molybdenum or a compound thereof dispersed on said support, wherein the support comprises an aluminosilicate zeolite combined with a binder selected from silica, titania, zirconia and mixtures thereof.

Conveniently, the catalyst is substantially free of reactive aluminum external to the framework of said aluminosilicate zeolite.

In still yet a further aspect, the invention resides in a process for converting methane to higher hydrocarbons including aromatic hydrocarbons, the process comprising contacting a feed comprising methane with a dehydrocyclization catalyst in a reaction zone under conditions effective to convert said methane to aromatic hydrocarbons, said dehydrocyclization catalyst comprising molybdenum supported on particles having an average size between about 50 and about 5000 μm, and a density between about 100 and about 200 $lb/ft^3$.

DETAILED DESCRIPTION OF THE EMBODIMENTS

As used herein the term "higher hydrocarbon(s)" means hydrocarbon(s) having more than one carbon atom per molecule, e.g., ethane, ethylene, propane, propylene, benzene, toluene, xylenes, naphthalene, and/or methyl naphthalene.

As used herein the term "aromatic hydrocarbon(s)" means molecules containing one or more aromatic rings. Examples of aromatic hydrocarbons are benzene, toluene, xylenes, naphthalene, and methylnaphthalenes.

The terms "coke" and "carbonaceous material" are used herein interchangeably to mean carbon containing materials, which are essentially non-volatile solids at the reaction conditions, with a low hydrogen content relative to carbon content (such as a H/C molar ratio of less than 0.8; most probably less than 0.5). These may include crystalline graphite, graphitic sheets, graphitic fragments, amorphous carbon, or other carbon containing structures which are essentially non-volatile solids at the reaction conditions.

The present invention provides a catalyst and process for the conversion of methane to higher hydrocarbons including aromatic hydrocarbons. The catalyst comprises molybdenum or a compound thereof dispersed on a support and hence, as used herein the term "catalyst" means the combination of (a) molybdenum or a compound thereof and (b) a support. The support employed in the present catalyst comprises an aluminosilicate zeolite combined with a binder typically selected from silica, titania, zirconia and mixtures thereof. In some embodiments the catalyst can also include a filler or densifying agent separate from the zeolite and binder. Thus, as used herein the term "support" means the combination of (a) an aluminosilicate zeolite, (b) a binder and, optionally, (c) a filler.

By using a catalyst that is substantially free of reactive aluminum external to the framework of the aluminosilicate zeolite, such as the aluminum contained in an alumina binder, it is found that the formation of undesirable aluminum molybdate during production and use of the catalyst can be mitigated, thereby reducing the coke selectivity of the catalyst.

The conversion of methane to aromatics generates hydrogen as a by-product and hence the present process also includes one or more hydrogen rejection steps in which at least part of the hydrogen by-product is converted to higher value products.

Feedstock

Any methane-containing feedstock can be used in the present process but in general the process is intended for use with a natural gas feedstock. Other suitable methane-containing feedstocks include those obtained from sources such as coal beds, landfills, agricultural or municipal waste fermentation, and/or refinery gas streams.

Methane-containing feedstocks, such as natural gas, typically contain carbon dioxide and ethane in addition to methane. Ethane and other aliphatic hydrocarbons that may be present in the feed can be converted directly to aromatics products in the dehydrocyclization step. In addition, as will be discussed below, carbon dioxide can be converted to useful aromatics products either directly in the dehydrocyclization step or indirectly through conversion to methane and/or ethane in a hydrogen rejection step.

Nitrogen and/or sulfur impurities are also typically present in methane-containing streams and desirably are removed, or reduced to low levels, prior to use of the streams in the process of the invention. In an embodiment, the feed to the dehydrocyclization step contains less than 100 ppm, for example less than 10 ppm, such as less than 1 ppm each of nitrogen and sulfur compounds.

In addition, the feed to the dehydrocyclization step may contain at least one of hydrogen, water, oxygen, carbon monoxide and carbon dioxide in order to assist in coke mitigation. These additives can be introduced as separate co-feeds or can be present in the methane stream, such as, for example, where the methane stream is derived from natural gas containing carbon dioxide. Other sources of carbon dioxide may include flue gases, LNG plants, hydrogen plants, ammonia plants, glycol plants and phthalic anhydride plants.

In one embodiment, the feed to the dehydrocyclization step contains carbon dioxide and comprises about 90 to about 99.9 mol %, such as about 97 to about 99 mol %, methane and about 0.1 to about 10 mol %, such as about 1 to about 3 mol %, $CO_2$. In another embodiment, the feed to the dehydrocyclization step contains carbon monoxide and comprises about 80 to about 99.9 mol %, such as about 94 to about 99 mol %, methane and about 0.1 to about 20 mol %, such as about 1 to about 6 mol %, CO. In a further embodiment, the feed to the dehydrocyclization step contains steam and comprises about 90 to about 99.9 mol %, such as about 97 to about 99 mol %, methane and about 0.1 to about 10 mol %, such as about 1 to about 5 mol %, steam. In yet a further embodiment, the feed to the dehydrocyclization step contains hydrogen and comprises about 80 to about 99.9 mol %, such as about 95 to about 99 mol %, methane and about 0.1 to about 20 mol %, such as about 1 to about 5 mol %, hydrogen.

The feed to the dehydrocyclization step can also contain higher hydrocarbons than methane, including aromatic hydrocarbons. Such higher hydrocarbons can be recycled from a hydrogen rejection step, added as separate co-feeds or can be present in the methane stream, such as, for example, when ethane is present in a natural gas feed. Higher hydrocarbons recycled from a hydrogen rejection step typically include one-ring aromatics and/or paraffins and olefins having predominately 6 or less, such as 5 or less, for example 4 or less, typically 3 or less carbon atoms. In general, the feed to the dehydrocyclization step contains less than 5 wt %, such as less than 3 wt %, of $C_3$+ hydrocarbons.

Dehydrocyclization Catalyst

The dehydrocyclization catalyst employed herein comprises molybdenum or a compound thereof, such as molybdenum oxide or carbide, dispersed on a support comprising an aluminosilicate zeolite and a binder that is substantially free of aluminum. Conveniently, the molybdenum or compound thereof is present in an amount between about 0.1% and about 20%, such as between about 0.5% and about 10%, for example between 1% and 8%, based on elemental Mo by weight of the total catalyst. Moreover, in addition to the molybdenum, the catalyst can contain one or more other dehydrogenation metals, such as tungsten, zinc, and/or rhenium, or compounds thereof.

Suitable aluminosilicate zeolites for use in the support of the dehydrocyclization catalyst include materials having the framework types MFI (e.g., ZSM-5 and silicalite), MEL (e.g., ZSM-11), MTW (e.g., ZSM-12), TON (e.g., ZSM-22), MTT (e.g., ZSM-23), FER (e.g., ZSM-35), MFS (e.g., ZSM-57), MWW (e.g., MCM-22, PSH-3, SSZ-25, ERB-1, ITQ-1, ITQ-2, MCM-36, MCM-49 and MCM-56), IWR (e.g., ITQ-24), KFI (e.g., ZK-5), BEA (e.g., zeolite beta), ITH (e.g., ITQ-13), MOR (e.g., mordenite), FAU (e.g., zeolites X, Y, ultrastabilized Y and dealuminized Y), LTL (e.g., zeolite L), IWW (e.g., ITQ-22), and VFI (e.g., VPI-5), as well as materials such as MCM-68, EMM-1, EMM-2, ITQ-23, ITQ-24, ITQ-25, ITQ-26, ETS-2, ETS-10, SAPO-17, SAPO-34 and SAPO-35. Suitable mesoporous materials include MCM-41, MCM-48, MCM-50, FSM-16 and SBA-15.

Generally, the aluminosilicate zeolite employed herein has a Constraint Index between about 1 and about 12 (as defined in U.S. Pat. No. 4,016,218, which is incorporated herein by reference) and typically is ZSM-5. Conveniently, the aluminosilicate zeolite has a silica to alumina mole ratio between about 14 and about 500, such as between about 20 and about 300, for example between about 22 and about 280.

The zeolite can be modified by known methods, such as, for example, steaming, acid washing, caustic washing and/or treatment with silicon-containing compounds, phosphorus-containing compounds, and/or elements or compounds of Groups 1, 2, 3 and 13 of the Periodic Table of Elements. Such modifications can be used to alter the surface activity of the zeolite and hinder or enhance access to the internal pore structure of the zeolite.

In addition to the aluminosilicate zeolite, the catalyst support includes a binder, and optionally a filler, to provide the catalyst particles with the requisite size, density and hardness for use in the dehydroaromatization process. The binder is generally a refractory inorganic oxide, but should be substantially free fee of aluminum and hence suitable binders include silica, zirconia, titania and mixtures thereof. Generally, the binder is present in an amount between about 1 and about 90 weight %, such as between about 10 and about 90 weight %, for example between about 35 and about 85 weight %, of the support (binder plus zeolite).

The binder material can be amorphous, or it can be partly or wholly a crystalline or even a porous crystalline material, such as a zeolitic material. Thus, for example, it is known from U.S. Pat. Nos. 5,460,796 and 5,665,325, the entire contents of which are incorporated herein by reference, that an amorphous silica material, when present as a binder for a zeolite, can be crystallized to at least partly convert the binder into a zeolitic form, which may have the same or a different crystal structure that the core zeolite. Thus, in one embodiment, the aluminosilicate zeolite is ZSM-5 and the binder is silicalite.

The molybdenum component can be dispersed on the support by any means well known in the art such as co-precipitation, incipient wetness, evaporation, impregnation, spray-drying, sol-gel, ion-exchange, chemical vapor deposition, diffusion and physical mixing. In general, it is desirable to provide the molybdenum compound at the Bronsted acid sites of the aluminosilicate zeolite and hence the molybdenum compound can be dispersed on the zeolite before the zeolite is combined with the binder. Alternatively, the zeolite can be combined with the binder before the molybdenum compound is dispersed on the support.

Irrespective of how the molybdenum component is applied to the support, it is generally important to avoid exposure of the molybdenum containing catalyst to an oxygen-containing gas at a temperature in excess of 700° C., and preferably to avoid exposure to an oxygen-containing gas at a temperature in excess of 600° C. Thus, it has been found that in a high temperature oxidizing environment the molybdenum can react with aluminum present in the zeolite to produce bulk (that is not anchored to zeolite Bronsted acid sites) aluminum molybdate. Moreover, it has been found that this bulk aluminum molybdate can have a detrimental impact on the performance of the catalyst by increasing its coke selectivity. For example, where the molybdenum component is deposited on the zeolite support by impregnation of the support with a solution of a molybdenum compound, such as an ammonium heptamolybdate solution, the catalyst is normally subjected to a calcination step to convert the molybdenum compound the desired elemental or carbide form. If the calcination is conducted in air or other oxygen-containing gas, it is therefore desirable that the calcination temperature is less than or equal to 700° C., for example less than or equal to 540° C.

In some embodiments it may be desirable to include in the support a dense filler material, which is substantially inert to the conditions experienced in the dehydrocyclization reaction, so as to enhance thermal conductivity and heat capacity of the support as well as to increase its density. The filler material should also be substantially free of reactive aluminum. Suitable filler materials include silicon carbide and corundum. Conveniently, the filler material is present in an amount from about 0.1 to about 60%, such as about 20 to about 40% %, by weight of the support.

Typically the overall catalyst is present in the form of particles having an average particle size between about 50 and about 5000 µm, such as between about 100 and about 500 µm, generally about 300 µm, a particle density between about 100 and about 200 lb/ft$^3$, such as between about 130 and about 170 lb/ft$^3$, generally about 150 lb/ft$^3$, a high attrition resistance i.e. less than 1 wt % material attrited per pass through the reactor/regenerator system, preferably less than 0.01 wt % and a high heat capacity, namely greater 0.7 kilojoules/kg/° K, such as greater 0.9 kilojoules/kg/° K, for example greater 1.1 kilojoules/kg/° K. Heat capacity is defined as the quantity of energy adsorbed per unit mass per degree Kelvin.

Dehydrocyclization Process

In the dehydrocyclization step of the present process, the methane containing feedstock is contacted with the particulate dehydrocyclization catalyst under conditions, normally non-oxidizing conditions and typically reducing conditions, effective to convert the methane to higher hydrocarbons, including benzene and naphthalene. The principal net reactions involved are as follows:

(Reaction 1)

(Reaction 2)

(Reaction 3)

Carbon dioxide that may be present in the feed improves catalyst activity and stability by facilitating reactions such as:

(Reaction 4)

but negatively impacts equilibrium by allowing competing net reactions, such as;

(Reaction 5).

The dehydrocyclization step is conducted by contacting the methane-containing feedstock with the particulate dehydrocyclization catalyst in one or more fixed bed, moving bed or fluidized bed reaction zones. Generally, the feedstock is contacted in the or each reaction zone with a moving bed of dehydrocyclization catalyst, wherein the feedstock flows countercurrent to the direction of movement of the dehydrocyclization catalyst. In one embodiment, the or each reaction zone comprises a settling bed reactor, by which is meant a vertically disposed reactor in which particulate catalyst enters at or near the top of the reactor and flows under gravity to form a catalyst bed, while the feed enters the reactor at or near the base of the reactor and flows upwardly through the catalyst bed. In an alternative embodiment, the dehydrocyclization reaction is conducted in a plurality of series-connected fluidized bed reactors in which particulate catalyst is cascaded in one direction from one reactor to the next adjacent reactor in the series, while the feed is passed through and between the reactors in the opposite direction.

In some embodiments, a non-catalytic particulate material may be supplied to the dehydrocyclization reaction zone(s) in addition to the catalytic particulate material. The non-catalytic particulate material may be used as a material to transport energy (heat) into the system and/or to fill space as required providing the required hydrodynamic environment. The non-catalytic particulate material may form particulates without a binder or may be bound with an inorganic binder such as clay, silica, alumina, zirconia, or other metal oxide used to help maintain the physical integrity of the particles. Preferably the particles are of a substantially spherical shape. Examples of suitable non-catalytic particulate material are low surface area silica, alumina, ceramics, and silicon carbide.

Typically, the mass ratio of the flowrate of the catalytic particulate material plus any non-catalytic particulate material over the flowrate of the hydrocarbon feedstock in the or each dehydrocyclization reaction zone is from about 1:1 to about 100:1, such as from about 1:1 to about 40:1, for example from about 5:1 to 20:1.

The dehydrocyclization reaction is endothermic and hence the temperature in each dehydrocyclization reaction zone will tend to decrease from a maximum temperature to a minimum temperature as the reaction proceeds. Suitable conditions for the dehydrocyclization step include a maximum temperature of about 700° C. to about 1200° C., such as about 800° C. to about 950° C. and a minimum temperature of about 400° C. to about 800° C., such as about 500° C. to about 700° C. However, as will be discussed below, heat is supplied to the dehydrocyclization reaction to reduce the temperature drop during the reaction and hence, in some configurations, the difference between the maximum and minimum temperatures can be reduced to essentially zero. Alternatively, by supplying heated catalyst to the dehydrocyclization reaction, it is possible to produce an inverse temperature profile; that is with the process gas outlet reaction temperature being greater than the process gas inlet reaction temperature.

In one embodiment, the countercurrent flow of the feedstock and the particulate dehydrocyclization catalyst is arranged to produce an inverse temperature profile across dehydrocyclization reaction system, such that, despite the endothermic nature of the dehydrocyclization reaction, the difference between the reaction temperature of the gaseous effluent at the outlet from the dehydrocyclization reaction system and the reaction temperature of the methane-containing feed at the inlet to the dehydrocyclization reaction system is at least +10° C., such as at least +50° C., for example at least +100° C., and even at least +150° C.

In any event, since the dehydrocyclization reaction is endothermic, the catalytic particulate material enters the dehydrocyclization reaction system at a first, high temperature, typically about 800° C. to about 1200° C., such as about 900° C. to about 1100° C., and exits the reaction system at a second lower temperature, typically about 500° C. to about 800° C., such as about 600° C. to about 700° C. The total temperature difference of the catalytic particulate material across the reaction zones is at least 100° C.

Other conditions used in the dehydrocyclization reaction generally include a pressure of about 1 kPa to about 1000 kPa, such as about 10 to about 500 kPa, for example about 50 kPa to about 200 kPa and a weight hourly space velocity of about 0.01 to about 1000 $hr^{-1}$, such as about 0.1 to about 500 $hr^{-1}$, for example about 1 to about 20 $hr^{-1}$. Conveniently, the dehydrocyclization step is conducted in the absence of $O_2$.

The major components of the effluent from the dehydrocyclization step are hydrogen, benzene, naphthalene, carbon monoxide, ethylene, and unreacted methane. Typically, the effluent contains at least 5 wt. %, such as at least 10 wt. %, for example at least 20 wt. %, conveniently at least 30 wt. %, more aromatic rings than the feed.

The benzene and naphthalene are separated from the dehydrocyclization effluent, for example, by solvent extraction followed by fractionation, and can be recovered as a product stream. However, as will be discussed below, at least part of these aromatic components can be submitted to an alkylation step, before or after product recovery, to produce higher value materials, such as xylenes. Moreover, as will be discussed below, the present process utilizes the hydrogen generated as a by-product of the dehydrocyclization reaction and in particular converts at least part of the hydrogen to higher value products.

Catalyst Regeneration

Even using a non-aluminum containing binder, the dehydrocyclization reaction tends to deposit coke on the catalyst and hence, to maintain the activity of the catalyst, at least part of the catalyst is continuously or intermittently regenerated. This is typically achieved by withdrawing a portion of the catalyst from the or each reaction zone, either on an intermittent, or a continuous basis, and then transferring the catalyst portion to a separate regeneration zone. In the regeneration zone, the coked dehydrocyclization catalyst is contacted with a regeneration gas under conditions effective to remove at least a portion of the carbonaceous material on the catalyst. The regeneration zone may be a reactor operated as a fluidized bed, an ebulating bed, a settling bed, a riser reactor or a combination thereof. In practice, each regeneration zone may include a plurality of reactors, such as a plurality of riser reactors connected in parallel or a plurality of reactors connected in series such as a riser reactor followed by a settling bed. After regeneration the catalyst is returned to reaction zone.

In one embodiment, the regeneration is conducted in the presence of an oxygen-containing gas. Generally, the oxygen-containing gas contains less $O_2$ than air, such as less than 10 wt %, more preferably less than 5 wt %, $O_2$, and is preferably substantially free of $H_2O$. The regeneration gas may also contain $CO_2$ to gasify a portion of the coke from the catalyst. Convenient sources of the regeneration gas are an $O_2$ depleted, $N_2$ enriched stream from an air separation unit and a high $CO_2$ reject stream from industrial or natural gas processing to which air or $O_2$ has been added to achieve the target $O_2$ concentration. Suitable conditions for regeneration with an oxygen-containing gas include a temperature from about 400° C. to about 700° C., such as from about 550° C. to about 650° C., a pressure between 10 and 100 psia (69 and 690 kPa), such as between 15 and 60 psia (103 and 414 kPa), and a catalyst residence time between 0.1 and 100 minutes, such as between 1 and 20 minutes.

It will, however, be appreciated from the foregoing discussion that regeneration in an oxidizing environment can generate bulk aluminum molybdate and hence increase the coke selectivity of the regenerated catalyst. In general, therefore, it is preferable to conduct the regeneration in the presence of a hydrogen-containing gas whereby coke on the catalyst is converted to methane. Generally, the hydrogen-containing gas does not contain significant quantities of methane or other hydrocarbons; typically with the hydrocarbon content being less than 20 mol %, such as less than 10 mol %, for example less than 2 mol %. In one embodiment, the hydrogen required for the regeneration is obtained at least in part from the hydrogen-containing effluent from the dehydrocyclization reaction. Conveniently, hydrogen regeneration conditions comprise a temperature from about 700° C. to about 1200° C., such as from about 800° C. to about 1000° C., such as about 850° C. to about 950° C. and a pressure of at least 100 kPaa, such between about 150 kPaa and about 5000 kPaa.

Generally, the coked dehydrocyclization catalyst removed from the or each reaction zone will be at a lower temperature than the optimum for hydrogen regeneration and hence the removed catalyst is initially heated to the desired regeneration temperature by direct and/or indirect contact with combustion gases produced by combustion of a supplemental source of fuel. The heating is conducted in a heating zone which may be in the same vessel as the regeneration zone or which may be in a separate vessel from the regeneration zone. By "supplemental source of fuel" is meant that the source fuel is physically separate from the catalyst and hence is not, for example, coke generated on the catalyst as a by-product of the dehydrocyclization reaction. Typically, the supplemental source of fuel comprises a hydrocarbon, such as methane, and in particular a suitable fuel source is the natural gas used as the feedstock to the process. Conveniently, an oxygen-lean atmosphere is maintained in the heating zone so that burning the hydrocarbon fuel to heat the first catalyst portion produces synthesis gas, which can then be used to generate additional hydrocarbon product and/or fuel. In addition, in the case of direct heat transfer to the dehydrocyclization catalyst, the use of an oxygen-lean atmosphere minimizes the formation of aluminum molybdate as well as inhibiting oxidation of metal carbides present in the catalyst and reducing the average steam partial pressure and hence hydrothermal catalyst aging.

Alternatively, a suitable supplemental fuel source is hydrogen and, in particular, part of the hydrogen generated as a by-product of the aromatization reaction.

Catalyst Reheating

Since the dehydrocyclization reaction is endothermic, it is necessary to supply heat to the reaction. In the present process, this is conveniently achieved by withdrawing part of the catalyst from the reaction zone, either on an intermittent or a continuous basis, and transferring it to a separate heating zone, where the catalyst is heated by direct or indirect contact with hot combustion gases generated by burning a supplemental source of fuel. The heated catalyst is then returned to the reaction zone.

Where catalyst regeneration is effected in the presence of hydrogen, the preheating of the coked catalyst normally required to bring the catalyst to the optimum regeneration temperature may provide one possible route for supplying heat to the dehydrocyclization reaction. Similarly, oxidative regeneration is highly exothermic and can also be used to supply. However, to maintain heat balance using regeneration as the sole source of heat to the reaction, the process requires a high selectivity to coke rather than to the desired aromatic products. Thus, even, with oxidative regeneration, it will generally be desirable to employ a separate catalyst reheating step in addition to a catalyst regeneration step. Details of a method and apparatus for providing separate catalyst reheating and regeneration in the production of aromatics from methane can be found in US Published Patent Application No. 2007/0249740, the entire contents of which are incorporated herein by reference.

Catalyst Recarburizing

It will be appreciated that heating the dehydrocyclization catalyst for the purposes of regeneration and/or for heat transfer may subject the catalyst to oxidizing conditions, especially where catalyst heating involves direct contact with hot combustion gases. As a result, metals, such as rhenium, tungsten or molybdenum, present in the dehydrocyclization catalyst may be converted during the heating step from their catalytically active elemental or carbide form to an oxide species. Thus, before being returned to the reaction zone, the regenerated and/or reheated catalyst may be transferred to a catalyst treatment zone separate from the regeneration zone, the heating zone and the reaction zone, where the catalyst is contacted with a carburizing gas containing at least one hydrocarbon selected from methane, ethane, propane, butane, isobutene, hexane, benzene and naphthalene. In some cases, the carburizing gas may also contain at least one of $CO_2$, CO, $H_2$, $H_2O$ and inert diluents. Alternatively, the carburizing gas may be a mixture of hydrogen and at least one of CO and $CO_2$. Moreover, it may be desirable to contact the catalyst sequentially with a plurality of different carburizing gases, each comprising a hydrocarbon selected from methane, ethane, propane, butane, isobutene, hexane, benzene and naphthalene or a mixture of hydrogen and at least one of CO and $CO_2$.

To avoid damage to the catalyst, the carburization process is controlled so that the maximum temperature in the catalyst treatment zone is less than the maximum temperature in the dehydrocyclization reaction zone, although typically the maximum carburization temperature is higher than the maximum temperature reached in the regeneration zone. Generally the maximum temperature in the catalyst treatment zone is from about 400° C. to about 1100° C., such as from about 500° C. to about 900° C., with the minimum temperature being between 300° C. and 500° C. Typically, the catalyst treatment zone is operated at pressures between 10 and 100 psia (69 and 690 kPa), such as between 15 and 60 psia (103 and 414 kPa). Generally, the average residence time of catalyst particles in the catalyst treatment zone will be between 0.1 and 100 minutes, for example between 1 and 20 minutes. Under these conditions, the carburizing gas reacts with metal oxide species on the catalyst to return the metal to its catalytically active elemental or carbidic form. In addition, the carburizing gas can react with active surface sites on the catalyst support to decrease their tendency to generate coke in the dehydroaromatization reaction zone.

To maintain the temperature required for carburization of the regenerated catalyst, heat can supplied to the catalyst and/or the carburizing gas prior to or during the carburization step. For example heat can be supplied to the catalyst by indirect heating, by contacting with hot flue gas from the reaction zone or the heating zone, by contacting with the hot gaseous effluent from the carburization process, or by mixing with heated catalyst from the heating zone. Heat is conveniently supplied to the carburization gas by means of an external furnace or heat exchanger or by with heated catalyst from the heating zone.

In some cases, it may be desirable that the heated unregenerated catalyst is initially contacted with a $H_2$-rich stream to partially or fully reduce the metal component of the catalyst prior to the carburization step. It may also be desirable to subject the carburized catalyst to post treatment with $H_2$ and/or $CO_2$ to strip off any excess carbon that may have been deposited on the catalyst by the carburization step.

In practice, as the dehydrocyclization reaction proceeds, fresh dehydrocyclization catalyst will be added to the process either to make up for catalyst lost by mechanical attrition or deactivation and, although there are multiple means of addition of fresh catalyst, to avoid damage to the catalyst, it is generally desirable to add fresh catalyst to a region of the process that is operating at a temperature below the maximum temperature in each dehydrocyclization reaction zone. In one embodiment, fresh dehydrocyclization catalyst is added to the process by introduction into the catalyst treatment zone, whereby the fresh catalyst is contacted with the carburizing gas prior to transfer to the reaction zone for contact with the methane-containing feed. In another, embodiment the catalyst may be added to the lower temperature regions of a reactor system with an inverse temperature profile.

Hydrogen Management

Since hydrogen is a major component of the dehydrocyclization effluent, after recovery of the aromatic products, the effluent is subjected to a hydrogen rejection step to reduce the hydrogen content of the effluent before the unreacted methane is recycled to the dehydrocyclization step and to maximize feed utilization. Typically the hydrogen rejection step comprises reacting at least part of the hydrogen in the dehydrocyclization effluent with an oxygen-containing species, such as CO and/or $CO_2$, to produce water and a second effluent stream having a reduced hydrogen content compared with the first (dehydrocyclization) effluent stream. Suitable hydrogen rejection processes are described below and in our copending PCT Application Serial No. PCT/US2005/044042, filed on Dec. 2, 2005.

Conveniently, the hydrogen rejection step includes (i) methanation and/or ethanation, (ii) a Fischer-Tropsch process, (iii) synthesis of $C_1$ to $C_3$ alcohols, particularly methanol, and other oxygenates, (iv) synthesis of light olefins, paraffins and/or aromatics by way of a methanol or dimethyl ether intermediate and/or (v) selective hydrogen combustion. These steps may be employed sequentially to gain the greatest benefit; for example Fischer-Tropsch may first be employed to yield a $C_2$+ enriched stream followed by methanation to achieve high conversion of the $H_2$.

Typically, as described below, the hydrogen rejection step will generate hydrocarbons, in which case, after separation of the co-produced water, at least portion of the hydrocarbons are conveniently recycled to the dehydrocyclization step. For example, where the hydrocarbons produced in the hydrogen rejection step comprise paraffins and olefins, the portion recycled to the dehydrocyclization step conveniently comprises, paraffins or olefins with 6 or less carbon atoms, such as 5 or less carbon atoms, for example 4 or less carbon atoms or 3 or less carbon atoms. Where, the hydrocarbons produced in the hydrogen rejection step comprise aromatics, the portion recycled to the dehydrocyclization step conveniently comprises single ring aromatic species.

Methanation/Ethanation

In one embodiment the hydrogen rejection step comprises reaction of at least part of the hydrogen in the dehydrocyclization effluent with carbon dioxide to produce methane and/or ethane according to the following net reactions:

$$CO_2 + 4H_2 \leftrightarrow CH_4 + 2H_2O \quad \text{(Reaction 6)}$$

$$2CO_2 + 7H_2 \leftrightarrow C_2H_6 + 4H_2O \quad \text{(Reaction 7)}$$

The carbon dioxide employed is conveniently part of a natural gas stream and typically the same natural gas stream used as the feed to the dehydrocyclization step. Where the carbon dioxide is part of a methane-containing stream, the $CO_2:CH_4$ of the stream is conveniently maintained between about 1:1 and about 0.1:1. Mixing of the carbon dioxide-containing stream and the dehydrocyclization effluent is conveniently achieved by supplying the gaseous feeds to the inlet of a jet ejector.

The hydrogen rejection step to produce methane or ethane normally employs a $H_2:CO_2$ molar ratio close to the stoichiometric proportions required for the desired Reaction 6 or Reaction 7, although small variations can be made in the stoichiometric ratio if it is desired to produce a $CO_2$-containing or $H_2$-containing second effluent stream. The hydrogen rejection step to produce methane or ethane is conveniently effected in the presence of a bifunctional catalyst comprising a metal component, particularly a transition metal or compound thereof, on an inorganic support. Suitable metal components comprise copper, iron, vanadium, chromium, zinc, gallium, nickel, cobalt, molybdenum, ruthenium, rhodium, palladium, silver, rhenium, tungsten, iridium, platinum, gold, gallium and combinations and compounds thereof. The inorganic support may be an amorphous material, such as silica, alumina or silica-alumina, or like those listed for the dehydroaromatization catalyst. In addition, the inorganic support may be a crystalline material, such as a microporous or mesoporous crystalline material. Suitable porous crystalline materials include the aluminosilicates, aluminophosphates and silicoaluminophosphates listed above for the dehydrocyclization catalyst.

The hydrogen rejection step to produce methane and/or ethane can be conducted over a wide range of conditions including a temperature of about 100° C. to about 900° C., such as about 150° C. to about 500° C., for example about 200° C. to about 400° C., a pressure of about 200 kPa to about 20,000 kPa, such as about 500 to about 5000 kPa and a weight hourly space velocity of about 0.1 to about 10,000 hr$^{-1}$, such as about 1 to about 1,000 hr$^{-1}$. $CO_2$ conversion levels are typically between 20 and 100% and conveniently greater than 90%, such as greater than 99%. This exothermic reaction may be carried out in multiple catalyst beds with heat removal between beds. In addition, the lead bed(s) may be operated at higher temperatures to maximize kinetic rates and the tail beds(s) may be operated at lower temperatures to maximize thermodynamic conversion.

The main products of the reaction are water and, depending on the $H_2:CO_2$ molar ratio, methane, ethane and higher alkanes, together with some unsaturated $C_2$ and higher hydrocarbons. In addition, some partial hydrogenation of the carbon dioxide to carbon monoxide is preferred. After removal of the water, the methane, carbon monoxide, any unreacted carbon dioxide and higher hydrocarbons can be fed directly to the dehydrocyclization step to generate additional aromatic products.

Fischer-Tropsch Process

In another embodiment the hydrogen rejection step comprises reaction of at least part of the hydrogen in the dehydrocyclization effluent with carbon monoxide according to the Fischer-Tropsch process to produce $C_2$ to $C_5$ paraffins and olefins.

The Fischer-Tropsch process is well known in the art, see for example, U.S. Pat. Nos. 5,348,982 and 5,545,674 incorporated herein by reference. The process typically involves the reaction of hydrogen and carbon monoxide in a molar ratio of about 0.5:1 to about 4:1, such as about 1.5:1 to about 2.5:1, at a temperature of about 175° C. to about 400° C., such as about 180° C. to about 240° C. and a pressure of about 1 to about 100 bar (100 to 10,000 kPa), such as about 10 to about 40 bar (1,000 to 4,000 kPa), in the presence of a Fischer-Tropsch catalyst, generally a supported or unsupported Group VIII, non-noble metal, e.g., Fe, Ni, Ru, Co, with or without a promoter, e.g. ruthenium, rhenium, hafnium, zirconium, titanium. Supports, when used, can be refractory metal oxides such as Group IVB, i.e., titania, zirconia, or silica, alumina, or silica-alumina. In one embodiment, the catalyst comprises a non-shifting catalyst, e.g., cobalt or ruthenium, especially cobalt, with rhenium or zirconium as a promoter, especially cobalt and rhenium supported on silica or titania, generally titania.

In another embodiment, the hydrocarbon synthesis catalyst comprises a metal, such as Cu, Cu/Zn or Cr/Zn, on the ZSM-5 and the process is operated to generate significant quantities of single-ring aromatic hydrocarbons. An example of such a process is described in *Study of Physical Mixtures of $Cr_2O_3$—ZnO and ZSM-5 Catalysts for the Transformation of Syngas into Liquid Hydrocarbons* by Jose Erena; Ind. Eng. Chem. Res. 1998, 37, 1211-1219, incorporated herein by reference.

The Fischer-Tropsch liquids, i.e., $C_5+$, are recovered and light gases, e.g., unreacted hydrogen and CO, $C_1$ to $C_3$ or $C_4$ and water are separated from the heavier hydrocarbons. The heavier hydrocarbons can then be recovered as products or fed to the dehydrocyclization step to generate additional aromatic products.

The carbon monoxide required for the Fischer-Tropsch reaction can be provided wholly or partly by the carbon monoxide present in or cofed with the methane-containing feed and generated as a by-product in the dehydrocyclization step. If required, additional carbon monoxide can be generated by feeding carbon dioxide contained, for example, in natural gas, to a shift catalyst whereby carbon monoxide is produced by the reverse water gas shift reaction:

$$CO_2 + H_2 \leftrightarrow CO + H_2O \qquad \text{(Reaction 8)}$$

and by the following reaction:

$$CH_4 + H_2O \leftrightarrow CO + 3H_2$$

Alcohol Synthesis

In a further embodiment the hydrogen rejection step comprises reaction of at least part of the hydrogen in the dehydrocyclization effluent with carbon monoxide to produce $C_1$ to $C_3$ alcohols, and particularly methanol. The production of methanol and other oxygenates from synthesis gas is also well-known and is described in, for example, in U.S. Pat. Nos. 6,114,279; 6,054,497; 5,767,039; 5,045,520; 5,254,520; 5,610,202; 4,666,945; 4,455,394; 4,565,803; 5,385,949, the descriptions of which are incorporated herein by reference. Typically, the synthesis gas employed has a molar ratio of hydrogen ($H_2$) to carbon oxides ($CO+CO_2$) in the range of from about 0.5:1 to about 20:1, such as in the range of from about 2:1 to about 10:1, with carbon dioxide optionally being present in an amount of not greater than 50% by weight, based on total weight of the syngas.

The catalyst used in the methanol synthesis process generally includes an oxide of at least one element selected from the group consisting of copper, silver, zinc, boron, magnesium, aluminum, vanadium, chromium, manganese, gallium, palladium, osmium and zirconium. Conveniently, the catalyst is a copper based catalyst, such as in the form of copper oxide, optionally in the presence of an oxide of at least one element selected from silver, zinc, boron, magnesium, aluminum, vanadium, chromium, manganese, gallium, palladium, osmium and zirconium. Conveniently, the catalyst contains copper oxide and an oxide of at least one element selected from zinc, magnesium, aluminum, chromium, and zirconium. In one embodiment, the methanol synthesis catalyst is selected from the group consisting of: copper oxides, zinc oxides and aluminum oxides. More preferably, the catalyst contains oxides of copper and zinc.

The methanol synthesis process can be conducted over a wide range of temperatures and pressures. Suitable temperatures are in the range of from about 150° C. to about 450° C., such as from about 175° C. to about 350° C., for example from about 200° C. to about 300° C. Suitable pressures are in the range of from about 1,500 kPa to about 12,500 kPa, such as from about 2,000 kPa to about 10,000 kPa, for example 2, 500 kPa to about 7,500 kPa. Gas hourly space velocities vary depending upon the type of process that is used, but generally the gas hourly space velocity of flow of gas through the catalyst bed is in the range of from about $50\ hr^{-1}$ to about $50,000\ hr^{-1}$, such as from about $250\ hr^{-1}$ to about $25,000\ hr^{-1}$, for example from about $500\ hr^{-1}$ to about $10,000\ hr^{-1}$. This exothermic reaction may be carried out in either fixed or fluidized beds, including multiple catalyst beds with heat removal between beds. In addition, the lead bed(s) may be operated at higher temperatures to maximize kinetic rates and the tail beds(s) may be operated at lower temperatures to maximize thermodynamic conversion.

The resultant methanol and/or other oxygenates can be sold as a separate product, can be used to alkylate the aromatics generated in the dehydrocyclization step to higher value products, such as xylenes, or can be used as a feedstock for the production of lower olefins, particularly ethylene and propylene. The conversion of methanol to olefins is a well-known process and is, for example, described in U.S. Pat. No. 4,499, 327, incorporated herein by reference.

Selective Hydrogen Combustion

In yet another embodiment, the hydrogen rejection step comprises selective hydrogen combustion, which is a process in which hydrogen in a mixed stream is reacted with oxygen to form water or steam without substantially reacting hydrocarbons in the stream with oxygen to form carbon monoxide, carbon dioxide, and/or oxygenated hydrocarbons. Generally, selective hydrogen combustion is carried out in the presence of an oxygen-containing solid material, such as a mixed metal oxide, that will release a portion of the bound oxygen to the hydrogen.

One suitable selective hydrogen combustion process is described in U.S. Pat. No. 5,430,210, incorporated herein by reference, and comprises contacting at reactive conditions a first stream comprising hydrocarbon and hydrogen and a second stream comprising oxygen with separate surfaces of a membrane impervious to non-oxygen containing gases, wherein said membrane comprises a metal oxide selective for hydrogen combustion, and recovering selective hydrogen combustion product. The metal oxide is typically a mixed metal oxide of bismuth, indium, antimony, thallium and/or zinc.

U.S. Pat. No. 5,527,979, incorporated herein by reference, describes a process for the net catalytic oxidative dehydrogenation of alkanes to produce alkenes. The process involves simultaneous equilibrium dehydrogenation of alkanes to alkenes and the selective combustion of the hydrogen formed to drive the equilibrium dehydrogenation reaction further to the product alkenes. In particular, the alkane feed is dehydrogenated over an equilibrium dehydrogenation catalyst in a first reactor, and the effluent from the first reactor, along with oxygen, is then passed into a second reactor containing a metal oxide catalyst which serves to selectively catalyze the combustion of hydrogen. The equilibrium dehydrogenation catalyst may comprise platinum and the selective metal oxide combustion catalyst may contain bismuth, antimony, indium, zinc, thallium, lead and tellurium or a mixture thereof.

U.S. Patent Application Publication No. 2004/0152586, published Aug. 5, 2004 and incorporated herein by reference, describes a process for reducing the hydrogen content of the effluent from a cracking reactor. The process employs a catalyst system comprising (1) at least one solid acid cracking component and (2) at least one metal-based selective hydrogen combustion component consisting essentially of (a) a metal combination selected from the group consisting of: i) at least one metal from Group 3 and at least one metal from Groups 4-15 of the Periodic Table of the Elements; ii) at least one metal from Groups 5-15 of the Periodic Table of the Elements, and at least one metal from at least one of Groups 1, 2, and 4 of the Periodic Table of the Elements; iii) at least one metal from Groups 1-2, at least one metal from Group 3, and at least one metal from Groups 4-15 of the Periodic Table of the Elements; and iv) two or more metals from Groups 4-15 of the Periodic Table of the Elements; and (b) at least one of oxygen and sulfur, wherein the at least one of oxygen and sulfur is chemically bound both within and between the metals.

The selective hydrogen combustion reaction of the present invention is generally conducted at a temperature in the range of from about 300° C. to about 850° C. and a pressure in the range of from about 1 atm to about 20 atm (100 to 2000 kPa).

Aromatic Product Recovery/Treatment

In addition to hydrogen, the other major products of the dehydrocyclization step are benzene and naphthalene. These products can be separated from the dehydrocyclization effluent, typically by solvent extraction followed by fractionation, and then sold directly as commodity chemicals. Alternatively, some or all of the benzene and/or naphthalene can be alkylated to produce, for example, toluene, xylenes and alkyl naphthalenes and/or can be subjected to hydrogenation to produce, for example, cyclohexane, cyclohexene, dihydronaphthalene (benzylcyclohexene), tetrahydronaphthalene (tetralin), hexahydronaphthalene (dicyclohexene), octahydronaphthalene and/or decahydronaphthalene (decalin). Suitable alkylation and hydrogenation processes are described below and in more detail in our copending PCT Application Serial Nos. PCT/US2005/043523, filed on Dec. 2, 2005 and PCT/US2005/044038, filed on Dec. 2, 2005.

Aromatics Alkylation

Alkylation of aromatic compounds such as benzene and naphthalene is well known in the art and typically involves reaction of an olefin, alcohol or alkyl halide with the aromatic species in the gas or liquid phase in the presence of an acid catalyst. Suitable acid catalysts include medium pore zeolites (i.e., those having a Constraint Index of 2-12 as defined in U.S. Pat. No. 4,016,218), including materials having the framework types MFI (e.g., ZSM-5 and silicalite), MEL (e.g., ZSM-11), MTW (e.g., ZSM-12), TON (e.g., ZSM-22), MTT (e.g., ZSM-23), MFS (e.g., ZSM-57) and FER (e.g., ZSM-35) and ZSM-48, as well as large pore zeolites (i.e, those having a Constraint Index of less than 2) such as materials having the framework types BEA (e.g., zeolite beta), FAU (e.g., ZSM-3, ZSM-20, zeolites X, Y, ultrastabilized Y and dealuminized Y), MOR (e.g., mordenite), MAZ (e.g., ZSM-4), MEI (e.g., ZSM-18) and MWW (e.g., MCM-22, PSH-3, SSZ-25, ERB-1, ITQ-1, ITQ-2, MCM-36, MCM-49 and MCM-56).

In one embodiment of the present process, benzene is recovered from the dehydrocyclization effluent and then alkylated with an olefin, such as ethylene produced as a by-product of a hydrogen rejection step employing ethanation/methanation. Typical conditions for carrying out the vapor phase alkylation of benzene with ethylene include a temperature of from about 650 to 900° F. (343 to 482° C.), a pressure of about atmospheric to about 3000 psig (100 to 20,800 kPa), a WHSV based on ethylene of from about 0.5 to about 2.0 hr$^{-1}$ and a mole ratio of benzene to ethylene of from 1:1 to 30:1. Liquid phase alkylation of benzene with ethylene may be carried out at a temperature between 300 and 650° F. (150 to 340° C.), a pressure up to about 3000 psig (20,800 kPa), a WHSV based on ethylene of from about 0.1 to about 20 hr$^{-1}$ and a mole ratio of benzene to ethylene of from 1:1 to 30:1.

Conveniently, the benzene ethylation is conducted under at least partial liquid phase conditions using a catalyst comprising at least one of zeolite beta, zeolite Y, MCM-22, PSH-3, SSZ-25, ERB-1, ITQ-1, ITQ-2, ITQ-13, ZSM-5 MCM-36, MCM-49 and MCM-56.

The benzene ethylation can be conducted at the site of the dehydrocyclization/hydrogen rejection process or the benzene can be shipped to another location for conversion to ethylbenzene. The resultant ethylbenzene can then be sold, used as a precursor in, for example, the production of styrene or isomerized by methods well known in the art to mixed xylenes.

In another embodiment of the present process, the alkylating agent is methanol or dimethylether (DME) and is used to alkylate benzene and/or naphthalene recovered from the dehydrocyclization effluent to produce toluene, xylenes, methylnaphthalenes and/or dimethylnaphthalenes. Where the methanol or DME is used to alkylate benzene, this is conveniently effected in presence of catalyst comprising a zeolite, such as ZSM-5, zeolite beta, ITQ-13, MCM-22, MCM-49, ZSM-11, ZSM-12, ZSM-22, ZSM-23, ZSM-35, and ZSM-48, which has been modified by steaming so as to have a Diffusion Parameter for 2,2 dimethylbutane of about 0.1-15 sec$^{-1}$ when measured at a temperature of 120° C. and a 2,2 dimethylbutane pressure of 60 torr (8 kPa). Such a process is selective to the production of para-xylene and is described in, for example, U.S. Pat. No. 6,504,272, incorporated herein by reference. Where the methanol is used to alkylate naphthalene, this is conveniently effected in the presence of a catalyst comprising ZSM-5, MCM-22, PSH-3, SSZ-25, ERB-1, ITQ-1, ITQ-2, ITQ-13, MCM-36, MCM-49 or MCM-56. Such a process can be used to selectively produce 2,6-dimethylnaphthalene and is described in, for example, U.S. Pat. Nos. 4,795,847 and 5,001,295, incorporated herein by reference.

Where methanol or DME is used as an alkylating agent in the process of the invention, it can be provided as a separate feed to the process or can at least partly be generated in situ by adding a carbon dioxide-containing feed gas, such as a natural gas stream, to part or all of the effluent from the dehydrocyclization step. In particular, the dehydrocyclization effluent, prior to any separation of the aromatic components, can be fed to a reverse shift reactor and reacted with the carbon dioxide-containing feed under conditions to increase the carbon monoxide content of the effluent by reactions, such as Reactions 5 and 8 above.

In addition, methane and $CO_2$ and/or steam may be fed to a reverse shift reactor to generate syngas which can then be mixed with a portion of the dehydrocyclization effluent to adjust the $H_2/CO/CO_2$ ratios as required for the alkylation step.

Typically, the reverse shift reactor contains a catalyst comprising a transition metal on a support, such as Fe, Ni, Cr, Zn on alumina, silica or titania, and is operated under conditions including a temperature of about 500° C. to about 1200° C., such as about 600° C. to about 1000° C., for example about 700° C. to about 950° C. and a pressure of about 1 kPa to about 10,000 kPa, such as about 2,000 kPa to about 10,000 kPa, for example about 3000 kPa to about 5,000 kPa. Gas hourly space velocities may vary depending upon the type of process used, but generally the gas hourly space velocity of flow of gas through the catalyst bed is in the range of about 50 hr$^{-1}$ to about 50,000 hr$^{-1}$, such as about 250 hr$^{-1}$ to about 25,000 hr$^{-1}$, more for example about 500 hr$^{-1}$ to about 10,000 hr$^{-1}$.

The effluent from the reverse shift reactor can then be fed to an alkylation reactor operating under conditions to cause reactions such as the following to occur:

$$CO+2H_2 \leftrightarrow CH_3OH \quad \text{(Reaction 9)}$$

$$CH_3OH+C_6H_6 \rightarrow toluene+H_2O \quad \text{(Reaction 10)}$$

$$2CH_3OH+C_6H_6 \rightarrow xylenes+2H_2O \quad \text{(Reaction 11)}$$

Suitable conditions for such an alkylation reactor would include a temperature of about 100 to about 700° C., a pressure of about 1 to about 300 atmospheres (100 to 30,000 kPa), and a WHSV for the aromatic hydrocarbon of about 0.01 to about 100 hr$^{-1}$. A suitable catalyst would comprise a molecular sieve having a constraint index of 1 to 12, such as ZSM-5, typically together with one or metals or metal oxides, such as copper, chromium and/or zinc oxide.

Conveniently, where the alkylation catalyst includes a molecular sieve, the latter is modified to change its diffusion characteristics such that the predominant xylene isomer produced by Reaction 11 is paraxylene. Suitable means of diffusion modification include steaming and ex-situ or in-situ deposition of silicon compounds, coke, metal oxides, such as MgO, and/or P on the surface or in the pore mouths of the molecular sieve. Also preferred is that an active metal be incorporated into the molecular sieve so as to saturate more highly reactive species, such as olefins, which may be generated as by-products and which could otherwise cause catalyst deactivation.

The effluent from the alkylation reactor could then be fed to a separation section in which the aromatic products would initially be separated from the hydrogen and other low molecular weight materials, conveniently by solvent extraction. The aromatics products could then be fractionated into a benzene fraction, a toluene fraction, a C$_8$ fraction and a heavy fraction containing naphthalene and alkylated naphthalenes. The C$_8$ aromatic fraction could then be fed to a crystallization or sorption process to separate the valuable p-xylene component and the remaining mixed xylenes either sold as product or fed to an isomerization loop to generate more p-xylene. The toluene fraction could either be removed as saleable product, recycled to the alkylation reactor or fed to a toluene disproportionation unit, such as a selective toluene disproportionation unit for the preparation of additional p-xylene.

Aromatics Hydrogenation

In addition to or instead of the alkylation step, at least part of the aromatic components in the dehydrocyclization effluent can be hydrogenated to generate useful products such as cyclohexane, cyclohexene, dihydronaphthalene (benzylcyclohexene), tetrahydronaphthalene (tetralin), hexahydronaphthalene (dicyclohexene), octahydronaphthalene and/or decahydronaphthalene (decalin). These products can be employed as fuels and chemical intermediates and, in the case of tetralin and decalin, can be used as the solvent for extracting the aromatic components from the dehydrocyclization effluent.

The hydrogenation is conveniently, but not necessarily, conducted after separation of the aromatic components from the dehydrocyclization effluent and conveniently employs part of the hydrogen generated by the dehydrocyclization reaction. Suitable aromatic hydrogenation processes are well known in the art and typically employ a catalyst comprising Ni, Pd, Pt, Ni/Mo or sulfided Ni/Mo supported on alumina or silica support. Suitable operating conditions for the hydrogenation process include a temperature of about 300 to about 1,000° F. (150 to 540° C.), such as about 500 to about 700° F. (260 to 370° C.), a pressure of about 50 to about 2,000 psig (445 to 13890 kPa), such as about 100 to about 500 psig (790 to 3550 kPa) and a WHSV of about 0.5 to about 50 hr$^{-1}$, such as about 2 to about 10 hr$^{-1}$.

Partial hydrogenation to leave one or more olefinic carbon-carbon bonds in the product may also be desirable so as to produce materials suitable for polymerization or other downstream chemical conversion. Suitable partial hydrogenation processes are well known in the art and typically employ a catalyst comprising noble metals with ruthenium being preferred supported on metallic oxides, such as La$_2$O$_3$—ZnO. Homogeneous noble metal catalyst systems can also be used. Examples of partial hydrogenation processes are disclosed in U.S. Pat. Nos. 4,678,861; 4,734,536; 5,457,251; 5,656,761; 5,969,202; and 5,973,218, the entire contents of which are incorporated herein by reference.

An alternative hydrogenation process involves low pressure hydrocracking of the naphthalene component to produce alkylbenzenes over a catalyst such as sulfided Ni/W or sulfided Ni supported on an amorphous aluminosilicate or a zeolite, such as zeolite X, zeolite Y or zeolite beta. Suitable operating conditions for low pressure hydrocracking include a temperature of about 300 to about 1,000° F. (150 to 540° C.), such as about 500 to about 700° F. (260 to 370° C.), a pressure of about 50 to about 2,000 psig (445 to 13890 kPa), such as about 100 to about 500 psig (790 to 3550 kPa) and a WHSV of about 0.5 to about 50 hr$^{-1}$, such as about 2 to about 10 hr$^{-1}$.

The invention will now be more particularly described with reference to the following non-limiting Examples.

Example 1

A Mo/ZSM-5 material was prepared for use in preparing bound catalyst particles. 1000 g of a commercially manufactured ZSM-5 having a silica to alumina mole ratio of 25:1 and a crystal size of about 0.5 micron was blended with 113.28 g of MoO$_3$ (Aldrich, 99.5%) for 2 hours in two batches. The batches were combined and calcined in a muffle furnace with flowing air for five hours at 500° C. with a heat-up ramp rate of 1° C./minute. The resulting Mo level was measured to be 6.7 wt % via XRF analysis.

Example 2

The material of Example 1 was used to prepare a 65 wt % MoZSM-5/35 wt % titania catalyst particle. 68.4 grams of the Mo/ZSM-5 were mulled with 35.9 g of titania (Degussa P-25) for 10 minutes. Water was added to produce a 65.7% solids mix. The material was extruded to 1/10" cylinder extrudate. The extrudate was dried and calcined in a muffle furnace for 6 hours at 1000° F. (540° C.) in flowing air with a heat up rate of 5° F. (3° C.)/minute. The resulting Mo level was measured to be 4.5 wt % via XRF analysis.

Example 3

The material of Example 1 was used to prepare a 80 wt % MoZSM-5/20 wt % titania catalyst particle. 84.2 grams of the Mo/ZSM-5 were mulled with 20.5 g of titania (Degussa P-25) for 10 minutes. Water was added to produce a ~65% solids mix. The material was extruded to 1/10" cylinder extrudate. The extrudate was dried and calcined in a muffle furnace for 6 hours at 1000° F. (540° C.) in flowing air with a heat up rate of 5° F. (3° C.)/minute. The resulting Mo level was measured to be 5.0 wt % via XRF analysis.

Example 4

The material of Example 1 was used to prepare a 65 wt % MoZSM-5/35 wt % alumina catalyst particle. 68.4 grams of the Mo/ZSM-5 were mulled with 38.6 g of alumina (UOP Versal 300) for 10 minutes. Water was added to produce a 53.8% solids mix. The material was extruded to 1/10" cylinder extrudate. The extrudate was dried and calcined in a muffle furnace for 6 hours at 1000° F. (540° C.) in flowing air with a heat up rate of 5° F. (3° C.)/minute. The resulting Mo level was measured to be 4.0 wt % via XRF analysis.

Example 5

The material of Example 1 was used to prepare an 80 wt % MoZSM-5/20 wt % alumina catalyst particle. 84.2 grams of the Mo/ZSM-5 were mulled with 27.8 g of alumina (UOP Versal 300) for 10 minutes. Water was added to produce a 50.8% solids mix. The material was extruded to 1/10" cylinder extrudate. The extrudate was dried and calcined in a muffle furnace for 6 hours at 1000° F. (540° C.) in flowing air with a heat up rate of 5° F. (3° C.)/minute. The resulting Mo level was measured to be 5.1 wt % via XRF analysis.

Example 6

The material of Example 1 was used to prepare a 65 wt % MoZSM-5/35 wt % silica catalyst particle. 64.8 grams of the Mo/ZSM-5 were mulled with 43.8 g of silica (Grace Davison Ludox HS-40), 19.2 g of silica (Degussa, UltraSil VN3-SP) and 1.96 g of caustic solution at 10 minute intervals. Water was added to produce a 75.2% solids mix. The material was extruded to 1/10" cylinder extrudate. The extrudate was dried and calcined in a muffle furnace for 6 hours at 1000° F. (540° C.) in flowing air with a heat up rate of 5° F. (3° C.)/minute. The resulting Mo level was measured to be 4.6 wt % via XRF analysis.

Example 7

The material of Example 1 was used to prepare an 80 wt % MoZSM-5/20 wt % silica catalyst particle. 85 grams of the Mo/ZSM-5 were mulled with 25 g of silica (Grace Davison Ludox HS-40), 11 g of silica (Degussa, UltraSil VN3-SP) and 1.96 g of caustic solution at 10 minute intervals. Water was added to produce a 68.9% solids mix. The material was extruded to 1/10" cylinder extrudate. The extrudate was dried and calcined in a muffle furnace for 6 hours at 1000° F. (540° C.) in flowing air with a heat up rate of 5° F. (3° C.)/minute. The resulting Mo level was measured to be 5.5 wt % via XRF analysis.

Example 8

The material of Example 1 was used to prepare a 65 wt % MoZSM-5/35 wt % zirconia catalyst particle. 68.4 grams of the Mo/ZSM-5 were mulled with 35 g of zirconium (IV) oxide (Aldrich, 99%) for 10 minutes. Water was added to produce a 68.6% solids mix. The material was extruded to 1/10" cylinder extrudate. The extrudate was dried and calcined in a muffle for 6 hours at 1000° F. (540° C.) in flowing air with a heat up rate of 5° F. (3° C.)/minute. The resulting Mo level was measured to be 4.0 wt % via XRF analysis.

Example 9

The material of Example 1 was used to prepare a 80 wt % MoZSM-5/20 wt % zirconia catalyst particle. 84.2 grams of the Mo/ZSM-5 were mulled with 20 g of zirconium (IV) oxide (Aldrich, 99%) for 10 minutes. Water was added to produce a 63.8% solids mix. The material was extruded to 1/10" cylinder extrudate. The extrudate was dried and calcined in a muffle for 6 hours at 1000° F. (540° C.) in flowing air with a heat up rate of 5° F. (3° C.)/minute. The resulting Mo level was measured to be 5.2 wt % via XRF analysis.

Example 10

The material of Example 1 was used to prepare a 65 wt % MoZSM-5/15% silicon carbide/20 wt % silica catalyst particle. 69.3 grams of the Mo/ZSM-5 were mulled with 25 g of silica (Grace Davison Ludox HS-40), 11 g of silica (Degussa, UltraSil VN3-SP) and 15 g of silicon carbide (Aldrich) at 10 minute intervals. Water was added to produce a 65% solids mix. The material was extruded to 1/10" cylinder extrudate. The extrudate was dried and calcined in a muffle furnace for 6 hours at 1000° F. (540° C.) in flowing air with a heat up rate of 5° F. (3° C.)/minute. The resulting Mo level was measured to be 4.7 wt % via XRF analysis.

Example 11

The material of Example 1 was used to prepare a 65 wt % MoZSM-5/15% silicon carbide/20 wt % titania catalyst particle. 44.68 grams of the Mo/ZSM-5 were mulled with 13.44 g of titania (Degussa, P-25) and 9.9 g of silicon carbide (Aldrich) at 10 minute intervals. Water was added to produce a 65.7% solids mix. The material was extruded to 1/10" cylinder extrudate. The extrudate was dried and calcined in a muffle furnace for 6 hours at 1000° F. (540° C.) in flowing air with a heat up rate of 5° F. (3° C.)/minute. The resulting Mo level was measured to be 4.8 wt % via XRF analysis.

Example 12

250.8 grams of a commercially manufactured ZSM-5 having a silica to alumina mole ratio of 80:1 was mulled with 247.8 grams of Nalco AG colloidal silica, 23.6 grams of Aerosol silica and 1.74 grams of Methocel methyl cellulose. Water was added and the resultant mixture was extruded into a 2 mm diameter cylindrical extrudate. The resultant extrudate was dried at 120° C. for 15 hours and then calcined at 550° C. for 24 hours.

30 grams of the resultant silica bound ZSM-5 was heated to 950° F. (510° C.) at a 5° F. (3° C.)/min ramp rate in nitrogen and held for 3 hours. The material was twice exchanged with 5 ml of 1N $NH_4NO_3$ solution/gram of crystal for one hour, then dried and calcined in air for 6 hours at 1000° F. (540° C.) at a 5° F. (3° C.)/min ramp rate. The processed material, having a core crystal size of 2.3 microns was impregnated with 4.14 grams of ammonium molybdate tetrahydrate. The material was calcined in a muffle in flowing air all with 5° C. ramp rates for 2 hours at 70° C., then 2 hours at 120° C. and then 5 hours at 500° C. The resulting Mo level was measured to be 6.0 wt % via XRF analysis.

Example 13

30 grams of the unbound commercially manufactured ZSM-5 crystals (silica to alumina mole ratio of 80:1) used as the starting material in Example 12 were heated to 950° F. (510° C.) at a 5° F. (3° C.)/min ramp rate in nitrogen and held for 3 hours. The crystals were twice exchanged with 5 ml of 1N NH$_4$NO$_3$ solution/gram of crystal for one hour. The crystal was dried and calcined in air for 6 hours at 1000° F. (540° C.) at a 5° F. (3° C.)/min ramp rate. The resulting crystals, having a Si/Al$_2$ of 80 and a crystal size of 2.3 microns were impregnated with 4.14 grams of ammonium molybdate tetrahydrate. The material was calcined in a muffle in flowing air all with 5° C. ramp rates for 2 hours at 70° C., then 2 hours at 120° C. and then 5 hours at 500° C. The resulting Mo level was measured to be 6.0 wt % via XRF analysis.

Example 14

121 grams of the silica bound ZSM-5 extrudate produced in Example 12, and in the dried and calcined state, were placed in an autoclave together with 2.3 grams of sodium hydroxide, 16 grams of tetrapropyl ammonium bromide and 131.4 grams of water. The autoclave was closed and heated in 2 hours to 150° C. and then maintained at this temperature for 80 hours. The resultant zeolite bound ZSM-5 was removed from the autoclave and washed with demineralized water until the conductivity of the wash liquid was less than 100 microS/cm.

31.25 grams of the washed zeolite bound ZSM-5 were heated to 950° F. (510° C.) at a 5° F. (3° C.)/min ramp rate in nitrogen and held for 3 hours. The product was twice exchanged with 5 ml of 1N NH$_4$NO$_3$ solution/gram of product for one hour and then, after drying, was dried calcined in air for 6 hours at 1000° F. (540° C.) at a 5° F. (3° C.)/min ramp rate. The resulting catalyst, having a core crystal size of 2.3 microns and a binding crystal size of <0.5 microns, was impregnated with 4.14 grams of ammonium molybdate tetrahydrate. The material was calcined in a muffle in flowing air all with 5° C. ramp rates for 2 hours at 70° C., then 2 hours at 120° C. and then 5 hours at 500° C. The resulting Mo level was measured to be 6.0 wt % via XRF analysis.

Example 15

Each of the materials described above were sized to 20/40 mesh, diluted with 25 to 35 vol % quartz and formed into a catalyst bed having a length of 6 cm and a diameter of 0.6 cm (length to diameter ratio of 10). Each catalyst was then evaluated for first cycle performance in the dehydrocylization of methane. In each case, the catalyst was first activated under conditions of 15% CH$_4$—H$_2$, ramp from 120° C. to 800° C. at 5° C./min and hold for 0.5 hr (15000 mL CH$_4$—H$_2$/g catalyst/hr to form Mo$_2$C. The conditions of the catalytic evaluation were 800° C.; 2% CO$_2$, 10% H$_2$, 4.5% Ar, balance CH$_4$ at WHSV on CH$_4$=4. The materials were all compared consistently at 4 WHSV based on the active Mo/ZSM-5 weight in the catalyst. The results are shown in FIGS. 1 to 5.

Figure 1:
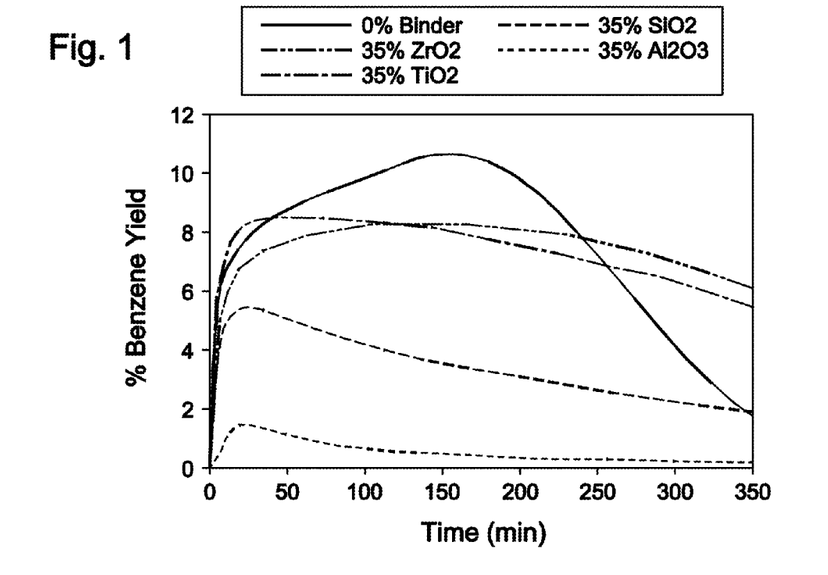
FIG. 1 is a graph comparing the benzene yield against time for the unbound Mo/ZSM-5 catalyst of Example 1 and the bound Mo/ZSM-5 catalysts (35 wt % binder in the catalyst) of Examples 2, 4, 6 and 8 when used in the dehydrocyclization of methane according to the process of Example 15.

In FIG. 1, the benzene selectivities of the 65 wt % MoZSM-5/35 wt % binder materials of Examples 2, 4, 6, and 8 are compared with that of the neat, unbound Mo/ZSM-5 of Example 1. In the area of interest, at low time on stream (<50 minutes), the zirconia and titania bound materials were found have benzene selectivity comparable that of the neat Mo/ZSM-5 but more stable during a single cycle, although the titania bound sample declines in performance with multiple regeneration cycles (not shown). The alumina bound catalyst shows poor performance; it is contemplated that the formation of aluminum molybdate, which is an active coke producer, decreases the molybdenum available to form molybdenum carbide in the activation step. Silica is seen to have intermediate performance.

Figure 2:
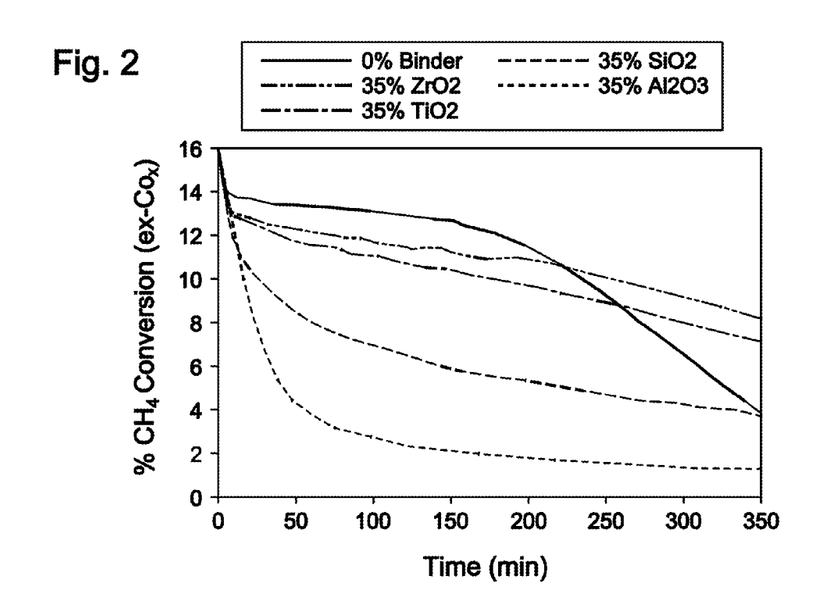
FIG. 2 is a graph comparing the methane conversion against time for the unbound Mo/ZSM-5 catalyst of Example 1 and the bound Mo/ZSM-5 catalysts (35 wt % binder in the catalyst) of Examples 2, 4, 6 and 8 when used in the dehydrocyclization of methane according to the process of Example 15.

In FIG. 2, the four 65 wt % MoZSM-5/35 wt % binder materials of Examples 2, 4, 6, and 8 are compared to the neat Mo/ZSM-5 Example 1 for CH$_4$ conversion. Similar to the results seen for the benzene yield data, the zirconia and titania bound materials have comparable conversion to the neat Mo/ZSM-5 but are more stable during a single cycle. The alumina bound material shows poor performance. The silica bound material showed conversion intermediate between the zirconia and titania and the alumina bound materials.

Figure 3:
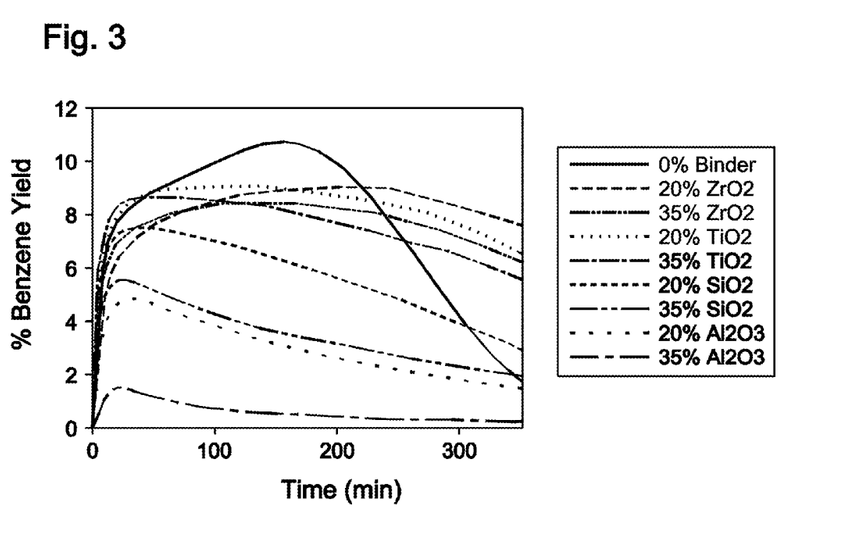
FIG. 3 is a graph comparing the benzene yield against time for the unbound Mo/ZSM-5 catalyst of Example 1, the bound Mo/ZSM-5 catalysts (35 wt % binder in the catalyst) of Examples 2, 4, 6 and 8 and the bound Mo/ZSM-5 catalysts (20 wt % binder in the catalyst) of Examples 3, 5, 7 and 9 when used in the dehydrocyclization of methane according to the process of Example 15.

In FIG. 3, the benzene selectivities of the 65 wt % MoZSM-5/35 wt % binder materials of Examples 2, 4, 6, and 8 are compared with those of the 80 wt % MoZSM-5/20t % binder materials of Examples 3, 5, 7, and 9 and that of the neat Mo/ZSM-5 of Example 1. The results for the 80 wt % Mo/ZSM-5 materials mirror those of the 65 wt % materials, confirming the positive performance achieved with both zirconia and titania. Use of either less alumina or less silica improves the performance of the catalyst.

Figure 4:
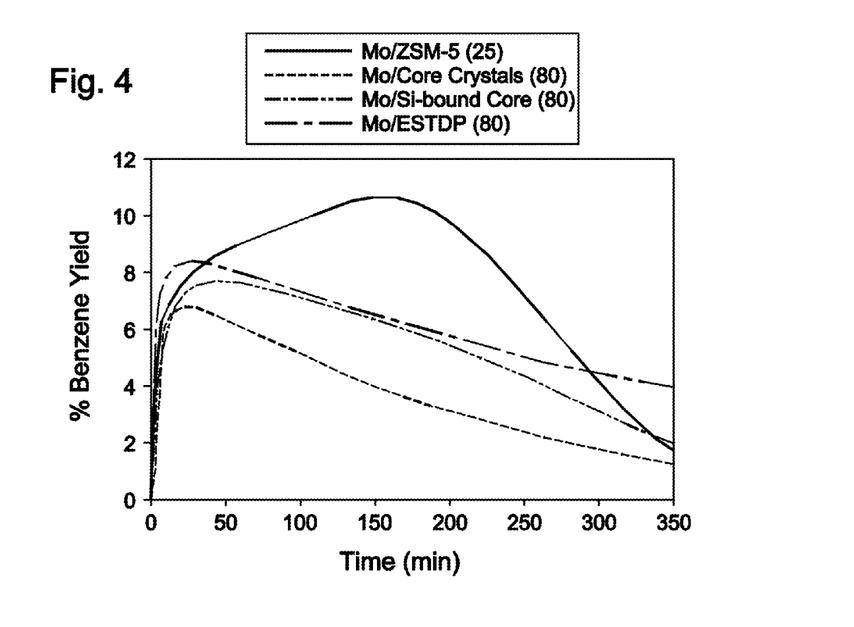
FIG. 4 is a graph comparing the benzene yield against time for the unbound Mo/ZSM-5 (silica to alumina mole ratio of 25) catalyst of Example 1 and the unbound and silica bound Mo/ZSM-5 (silica to alumina mole ratio of 80) catalysts of Examples 12, 13 and 14 when used in the dehydrocyclization of methane according to the process of Example 15.

In FIG. 4, the catalytic performance of the Mo/25:1 silica to alumina mole ratio ZSM-5 of Example 1 is compared to the performance of the Mo/80:1 silica to alumina mole ratio ZSM-5 of Example 12, the Mo/amorphous silica bound 80:1 silica to alumina mole ratio ZSM-5 of Example 13, and the Mo/zeolite bound 80:1 silica to alumina mole ratio ZSM-5 of Example 14. At the time of interest, <50 minutes, the two materials containing silica binder material, the catalysts of Examples 13 and 14, show benzene yields similar to that of the unbound Mo/ZSM-5 of Example 1. Given that the core ZSM-5 crystals of the catalysts of Examples 13 and 14 are much larger than the ZSM-5 crystals used in Example 1, this is a very encouraging result.

Figure 5:
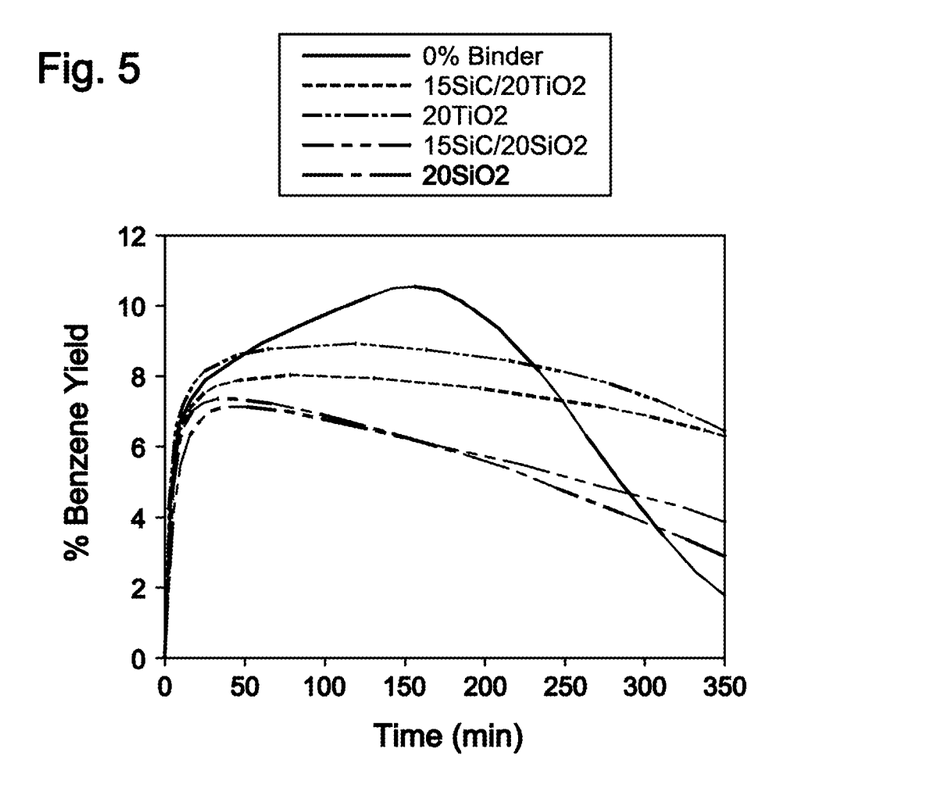
FIG. 5 is a graph comparing the benzene yield against time for the unbound Mo/ZSM-5 catalyst of Example 1, the titania and silica bound Mo/ZSM-5 catalysts of Examples 3 and 7 and the titania and silica bound Mo/SiC/ZSM-5 catalysts of Examples 10 and 11 when used in the dehydrocyclization of methane according to the process of Example 15.

In FIG. 5, the catalytic performance of the titania and silica bound materials of Examples 3 and 7 are compared with the performance of the equivalent materials containing 15 wt % silicon carbide, Examples 10 and 11, and that of the neat Mo/ZSM-5 of Example 1. In the time scale of interest, <50 minutes, the presence of silicon carbide in the catalyst particle does not significantly impact performance. Silicon carbide may provide advantages in density, thermal conductivity, and heat capacity of the catalyst particle.

Alternative Embodiments

1. A catalyst comprising a support and molybdenum or a compound thereof dispersed on the support, wherein the support comprises an aluminosilicate zeolite combined with a binder selected from silica, titania, zirconia and mixtures thereof, and wherein the catalyst is substantially free of aluminum external to the framework of the aluminosilicate zeolite.

2. The catalyst of paragraph 1 wherein the aluminosilicate zeolite has a silica to alumina mole ratio between about 14 and about 500.

3. The catalyst of paragraph 1 or paragraph 2 wherein the aluminosilicate zeolite has a Constraint Index between about 1 and about 12.

4. The catalyst of any preceding paragraph wherein the aluminosilicate zeolite comprises ZSM-5.

5. The catalyst of any preceding paragraph and comprising from about 0.1 to about 20% molybdenum or the compound thereof, calculated as elemental molybdenum, by weight of the total catalyst.

6. The catalyst of any preceding paragraph and comprising from about 1 to about 90% of the binder by weight of the support.

7. The catalyst of any preceding paragraph wherein the binder is a porous crystalline material.
8. The catalyst of any preceding paragraph wherein the support further comprises a filler separate from the binder and the aluminosilicate zeolite.
9. The catalyst of paragraph 8 wherein the filler is present in an amount from about 0.1 to about 60% by weight of the support.
10. A process for converting methane to higher hydrocarbons including aromatic hydrocarbons, the process comprising contacting a feed comprising methane with a dehydrocyclization catalyst in a reaction zone under conditions effective to convert the methane to aromatic hydrocarbons, the dehydrocyclization catalyst comprising a support and molybdenum or a compound thereof dispersed on the support, wherein the support comprises an aluminosilicate zeolite combined with a binder, and wherein the binder is substantially free of aluminum.
11. A process for converting methane to higher hydrocarbons including aromatic hydrocarbons, the process comprising contacting a feed comprising methane with a dehydrocyclization catalyst in a reaction zone under conditions effective to convert the methane to aromatic hydrocarbons, the dehydrocyclization catalyst comprising a support and molybdenum or a compound thereof dispersed on the support, wherein the support comprises an aluminosilicate zeolite combined with a binder selected from silica, titania, zirconia and mixtures thereof.
12. The process of paragraph 10 or paragraph 11 wherein the catalyst is substantially free of aluminum external to the framework of aluminosilicate zeolite.
13. The process of any one of paragraphs 10 to 12 wherein the aluminosilicate zeolite has a silica to alumina mole ratio between about 14 and about 500.
14. The process of any one of paragraphs 10 to 13 wherein the aluminosilicate zeolite has a Constraint Index between about 1 and about 12.
15. The process of any one of paragraphs 10 to 14 wherein the aluminosilicate zeolite comprises ZSM-5.
16. The process of any one of paragraphs 10 to 15 wherein the catalyst comprises from about 0.1 to about 20% molybdenum or the compound thereof, calculated as elemental molybdenum, by weight of the total catalyst.
17. The process of any one of paragraphs 10 to 16 wherein the support comprises from about 1 to about 90% of the binder by weight of the support.
18. The process of any one of paragraphs 10 to 17 wherein the support further comprises a filler separate from the binder and the aluminosilicate zeolite.
19. The catalyst of paragraph 18 wherein the filler is present in an amount from about 0.1 to about 60% by weight of the support.
20. A process for converting methane to higher hydrocarbons including aromatic hydrocarbons, the process comprising contacting a feed comprising methane with a dehydrocyclization catalyst in a reaction zone under conditions effective to convert the methane to aromatic hydrocarbons, the dehydrocyclization catalyst comprising molybdenum supported on particles having an average size between about 50 and about 5000 μm, and a density between about 100 and about 1000 lb/ft$^3$.
21. The process of paragraph 20 wherein the particles have an average size between about 100 and about 500 μm.
22. The process of paragraph 20 or paragraph 21 wherein the particles have a density between about 130 and about 170 lb/ft$^3$.
23. The process of any one of paragraphs 20 to 22 wherein the particles have a heat capacity greater 0.7 kilojoules/kg/° K.
24. The process of any one of paragraphs 20 to 22 wherein the support comprises an aluminosilicate zeolite combined with a binder.
25. The process of paragraph 24 wherein the binder is substantially free of aluminum.
26. The process of paragraph 24 or paragraph 25 wherein the binder is selected from silica, titania, zirconia and mixtures thereof.
27. The process of any one of paragraphs 24 to 26 wherein the support further comprises a filler separate from the binder and the aluminosilicate zeolite.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A catalyst for use in converting methane to aromatic hydrocarbons consisting essentially of a support and a metal dispersed on the support, said metal consisting of molybdenum and compounds thereof, wherein the support comprises aluminosilicate zeolite ZSM-5 combined with a binder selected from the group consisting of titania, zirconia, and mixtures thereof, and wherein the catalyst is substantially free of aluminum external to the framework of the aluminosilicate zeolite, said aluminosilicate having a silica to alumina mole ratio of between 14 and 500.

2. The catalyst of claim 1, wherein the aluminosilicate zeolite has a silica to alumina mole ratio between about 20 and about 300.

3. The catalyst of claim 1, further characterized as comprising from about 0.1 to about 20% molybdenum or the compound thereof, calculated as elemental molybdenum, by weight of the total catalyst.

4. The catalyst of claim 1, further characterized as comprising from about 1 to about 90% of the binder by weight of the support.

5. The catalyst of claim 1, wherein the binder is a porous crystalline material.

6. The catalyst of claim 1, further characterized as comprising molybdenum supported on particles having an average size between about 50 and about 5000 μm, and a density between about 100 and about 200 lb/ft$^3$.

7. The catalyst of claim 1, further comprising silicon carbide filler.

8. The catalyst of claim 1, wherein said binder comprises titania.

9. The catalyst of claim 1, wherein said binder comprises zirconia.

10. A catalyst for use in converting methane to aromatic hydrocarbons consisting essentially of a support and a metal dispersed on the support, said metal consisting of molybdenum and compounds thereof, wherein the support comprises ZSM-5 combined with a binder selected from the group consisting of titania, and mixtures thereof and a silicon carbide filler and wherein the catalyst is substantially free of aluminum and silica external to the framework of the aluminosilicate zeolite, said aluminosilicate having a silica to alumina mole ratio of between 14 and 500.

* * * * *